United States Patent [19]

Steer et al.

[11] 4,268,286

[45] May 19, 1981

[54] ATTACHABLE FILTER AND OSTOMY BAG INCLUDING SAME

[75] Inventors: Peter L. Steer; John V. Edwards, both of East Grinstead, England

[73] Assignee: Kingsdown Medical Consultants Limited, England

[21] Appl. No.: 171,676

[22] Filed: Jul. 24, 1980

[51] Int. Cl.[3] ......................... B01D 46/00; A61F 5/44
[52] U.S. Cl. ........................................ 55/278; 55/387; 55/493; 55/509; 55/DIG. 31; 55/385 C; 55/527; 128/283; 128/286
[58] Field of Search ..................... 55/278, DIG. 31, 2, 55/16, 387, 493, 509, 527, 385 C; 128/283, 286; 220/368, 371–374

[56] References Cited

U.S. PATENT DOCUMENTS

| | | |
|---|---|---|
| 2,496,175 | 1/1950 | Perry . |
| 2,555,086 | 5/1951 | Quinn . |
| 3,055,368 | 9/1962 | Baxter . |
| 3,089,493 | 5/1963 | Garlindo . |
| 3,439,677 | 4/1969 | Bonfils . |
| 3,759,260 | 9/1973 | Nolan et al. . |
| 3,804,091 | 4/1974 | Nolan et al. . |
| 3,865,109 | 2/1975 | Elmore et al. . |
| 3,881,250 | 5/1975 | Fredrickson .......................... 55/493 |
| 3,952,727 | 4/1976 | Nolan . |
| 4,120,715 | 10/1978 | Ockwell et al. ..................... 128/283 |
| 4,185,630 | 1/1980 | Neumeier et al. . |

FOREIGN PATENT DOCUMENTS

| | | |
|---|---|---|
| 1301101 | 12/1972 | United Kingdom . |
| 1541565 | 3/1979 | United Kingdom . |
| 2031282 | 4/1980 | United Kingdom . |

*Primary Examiner*—Bernard Nozick
*Attorney, Agent, or Firm*—Lawrence S. Levinson; Stephen B. Davis

[57] ABSTRACT

An attachable and detachable filter for use with an ostomy bag includes a plastics housing member having two sections hinged together by an integral hinge and each section has a peripheral wall. One section has at least one aperture in the wall and the other section carries a sharp-pointed resilient-headed generally cylindrical stud which is a push fit through the aperture in the other to clamp the two sections together. There is a layer of gas filtering material within one or both of the housing sections.

8 Claims, 7 Drawing Figures

ATTACHABLE FILTER AND OSTOMY BAG INCLUDING SAME

BACKGROUND OF THE INVENTION

Most ostomates employ some type of bag or pouch system to collect bodily wastes discharged from their surgically created stoma. Today, such pouches are generally formed of light weight, odor proof, flexbile polymeric materials and the collection systems are designed to be inconspicuous and permit the ostomate to engage in normal physical activity. However, many ostomates, particularly immediately following surgery, have fears concerning their ability to resume a "normal life". These fears center around worries that the collection system will leak or that odor will escape and that the system will be noticeable even through their outer clothing. Part of these problems are due to the discharge of flatus into the pouch which can cause an embarrassing distention of the pouch.

In order to overcome the problem of gas build up within the collecting system, it had been suggested to provide a vent opening either in the pouch or in the portion of the device which attaches to the body. Devices having simple vent openings are shown in U.S. Pat. Nos. 2,496,175; 3,055,368; 3,089,493; 3,865,109 and 4,185,630. Other devices have combined vent openings with filtering or deodorizing means as note U.S. Pat. Nos. 2,555,086; 3,439,677; 3,759,260; 3,804,091; 3,952,727 and British Pat. No. 1,541,565 and British Patent Application No. 2,031,282.

SUMMARY OF THE INVENTION

This invention relates to an attachable filter for an ostomy bag and to an ostomy bag including such a filter. The term "ostomy bag" is used to mean a colostomy or ileostomy or other kind of bag intended to be worn by a user to receive waste material expelled from the stoma.

According to the present invention, there is provided an attachable and detachable filter for use with an ostomy bag. The filter includes a plastics housing member having two sections hinged together by an integral hinge. Each section has a peripheral wall, one of these walls having at least one aperture therein and the other wall carrying at least one sharp-pointed resilient-headed stud which is a fit through the aperture in the other to clamp the two sections together. There is at least one layer of gas-filtering material contained within one or both housing sections.

The aperture may have an inwardly-extensing rib which is deformed by the stud as the stud is pushed in the aperture, and consequently grips the stud.

The gas filtering material may be carbon cloth such as that disclosed in British Pat. No. 1,301,101. Alternatively, it may be woven or non-woven fibrous material impregnated with activated carbon particles.

In use, the filter is applied to the ostomy bag by folding it over a top edge of the bag and forcing the pointed head of the stud through the two bag walls and then through the aperture in the other section clamping the filter together. This makes a hole in both the back and front bag walls at the upper region of the bag and any gas in the bag can pass out through one or other of these holes. The gas then arrives at the space around the stud within the two housings sections, and its only path to the exterior is past the gas filtering material and through the aperture or apertures in the peripheral wall. The gas filtering material serves to deodorize the issuing gas.

DETAILED DESCRIPTION OF THE INVENTION

Figure 1:
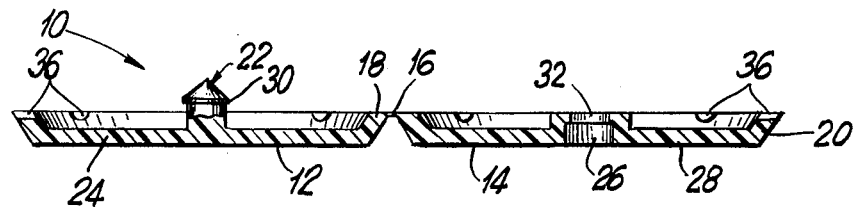
FIG. 1 is a central vertical section through a first embodiment of the filter of this invention shown in the open position.
Figure 2:
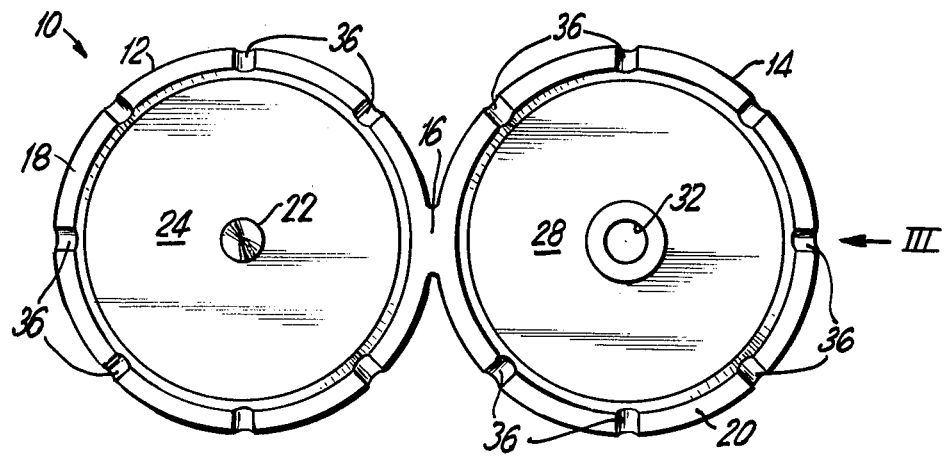
FIG. 2 is a plan view of the filter of FIG. 1.
Figure 3:
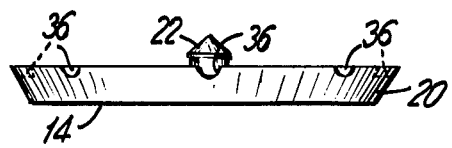
FIG. 3 is an end elevation looking in the direction III in FIG. 2.
Figure 4:
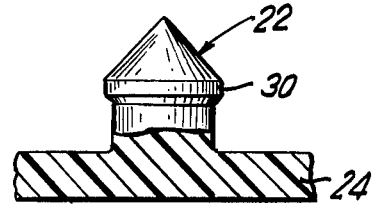
FIG. 4 is a detailed view on an enlarged scale showing a possible construction of the press stud.
Figure 5:
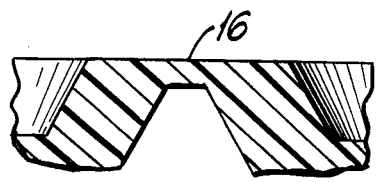
FIG. 5 is a detailed view on an enlarged scale showing a possible construction of the integral hinge.

A first embodiment of the attachable filter of this invention is shown in FIGS. 1 to 5. The filter includes a plastics housing member 10 having two sections 12 and 14 hinged together by an integral hinge 16, note FIG. 2, and each section has a peripheral wall 18, 20. The section 12 carries a sharp pointed resilient headed stud 22 which extends upwardly from the center of flat wall 24 of the first section. A corresponding recess or aperture 26 is provided at the center of flat wall 28 of second section 14. The head 22 of the stud is enlarged as shown at 30, note FIG. 4, and the stud is made of resilient material so that it can be forced through a neck portion 32 of the recess 26 and so hold the two sections 12 and 14 together in the closed position. As shown in FIGS. 1 to 3, each of sections 12 and 14 of the filter housing have radial apertures 36 therein. In use, these apertures function as gas exit apertures. Such apertures may be provided in the peripheral wall of only one of the two sections. Also, it may be sufficient to provide only one such aperture 36.

A layer of gas filtering material (not shown in FIGS. 1 to 3) is disposed within either or both filter housing sections 12 and 14. This material may for example be a woven or non-woven fibrous material impregnated with activated carbon particles or it may be a carbon cloth filtering material as described in British Pat. No. 1,301,101.

One suitable material for the housing 10 is a polypropylene copolymer, but the invention is not limited to the use of this material and it will be appreciated that other plastics materials are suitable. Also, although an integral hinge 16 has been described, it will be appreciated that alternatively a separate hinge could be fixed to each housing portion 12 and 14.

In use, the attachable filter housing is clipped over the top of an ostomy bag, with the pointed stud head 22 being forced through both the bags walls so making an orifice in each of them. The head 22 is forced into the recess 26, clamping the filter housing in a doubled over condition firmly clipped onto the ostomy bag. In this way, an orifice in each bag wall has been punctured and allows any gases in the ostomy bag to escape into the space defined between the closed housing sections 12 and 14. The gas can then pass to the exterior by traveling outwardly radially over or past the filtering material to the aperture 36. Thus, it is ensured that the escaping gases are deodorized since they are forced into contact with the filtering material over a considerable distance along their exit path.

Figure 6:
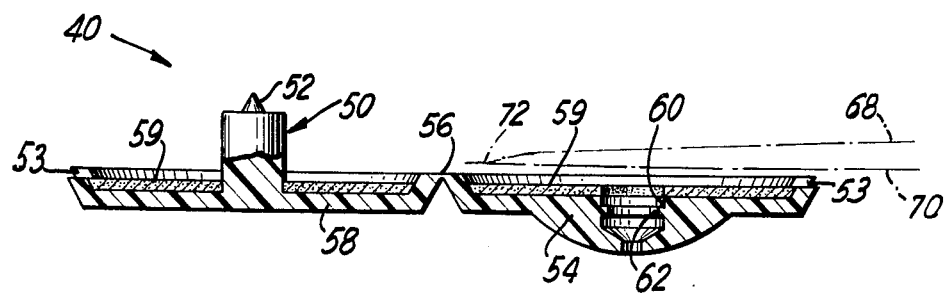
FIG. 6 is a section view similar to FIG. 1 of a second embodiment of the filter of this invention.
Figure 7:
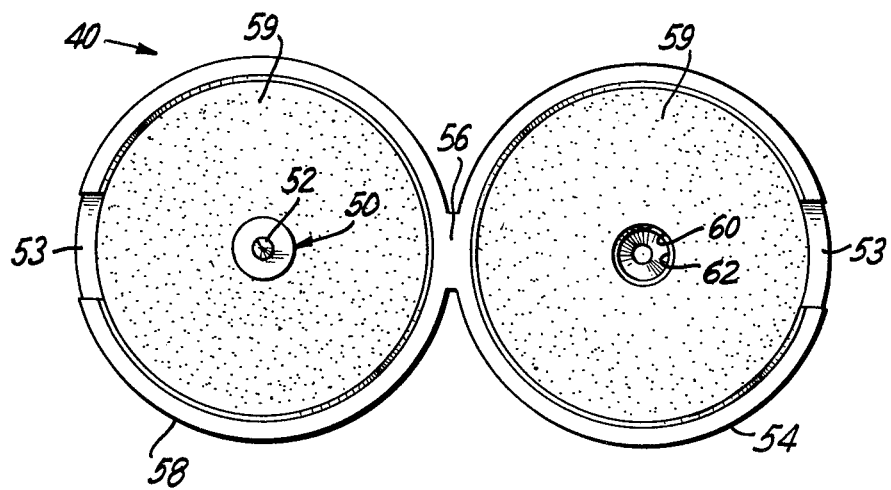
FIG. 7 is a plan view similar to FIG. 2 of the second embodiment.

A second embodiment of the attachable filter of this invention is illustrated in FIGS. 6 and 7. The filter includes a plastics housing member 40 having two sections 54 and 58 hinged together by an integral hinge 56. Section 58 carries a stud 50 having a cylindrical main body part and a pointed tip 52. Section 54 is provided with a recess or aperture 60 having an inwardly extending rib 62 which is deformable by the stud 50 when the two sections are closed together resulting in a gripping action on the cylindrical body part of the stud. The peripheral walls of sections 54 and 58 include portions 53 that are raised slightly to the same level as hinge 56. Thus when the filter is clamped into the closed position there will be a space through which gas can escape as was provided by apertures 36 in the previous embodiment.

The inwardly extending rib 62 may be molded during the manufacture of the housing such as by injection molding. However, instead of a peripheral rib, one may employ a number of bumps or projections extending inwardly an appropriate distance from the internal surface of the cylindrical wall of recess 60.

As in the first embodiment, either or both sections contain a layer of gas filtering material shown as 59 in the drawings. This material can be woven or non-woven fibrous material impregnated with activated carbon particles or it may be carbon cloth filtering material.

The filter housing of the second embodiment is clipped over the top of an ostomy bag in exactly the same manner as the housing of the first embodiment. FIG. 6 shows an ostomy bag having two walls 68 and 70 joined around their periphery to form a top edge 72. One of the walls 68 or 70 will have an adhesive face plate or other means for attaching the bag to the body of the ostomate around the stomal opening.

The filter arrangement of this invention has many advantages over those previously employed. It can be employed with any ostomy bag and does not require a bag of special construction. The filter is not attached to the bag by adhesive which can weaken and decrease in effectiveness over a period of time. The filter may be readily detached and, if desired, fitted to a new bag.

While there have been disclosed in the Figures a single sharp headed press stud and a single recess, it will be appreciated that more than one such stud and corresponding recess may be provided if desired. Naturally, while the first and second housing portions 12 and 14 and 54 and 58 have been shown as generally circular, they may be constructed of other shapes.

A slot, or more than one slot, may be provided in the shank of the stud 22 or 50 to allow gas passage in the event that the stud punches a hole in the bag wall whose edges closely embrace the stud shank.

What is claimed is:

1. An attachable and detachable filter for use with an ostomy bag, said filter comprising a plastics housing member having two sections, each of said sections having a peripheral wall, said sections being joined by an integral hinge between the top of said peripheral walls, one of said sections having at least one recess and the other section carrying at least one sharp-pointed and resilient-headed stud which is a push fit through said recess in the other to clamp together the two sections, there being at least one layer of gas filtering material contained within one or both of said housing sections.

2. The filter according to claim 1 in which said housing is made of polyproyplene copolymer.

3. The filter according to claim 1 in which said stud has a longitudinal slot in a shank portion thereof.

4. The filter according to claim 1 wherein said peripheral walls have apertures at their top edge except at the area of said hinge so that gas can escape across said filtering material and out through said aperture when the filter is in the clamped position.

5. The filter according to claim 1 wherein the filtering material is carbon cloth.

6. The filter according to claim 1 wherein said peripheral walls of both sections are at the same height as said integral hinge at only a portion of their circumference so that when said filter is clamped together gas can escape across said filtering material and out through the space between said peripheral walls.

7. The filter according to claim 6 wherein said stud is generally cylindrical and said recess has an inwardly extending rib.

8. The filter according to claim 6 wherein said stud is generally cylindrical and said recess has inwardly extending projections which grip said stud when the filter is closed.

* * * * *